United States Patent
Schaefer et al.

(10) Patent No.: US 8,481,798 B2
(45) Date of Patent: Jul. 9, 2013

(54) FEEDBACK AND FEEDFORWARD CLOSED LOOP PURITY AND RECOVERY CONTROL

(75) Inventors: Robert A. Schaefer, Houston, TX (US); Robert L. Long, Bayou Vista, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 13/321,627

(22) PCT Filed: Apr. 30, 2010

(86) PCT No.: PCT/US2010/033088
§ 371 (c)(1),
(2), (4) Date: Jan. 19, 2012

(87) PCT Pub. No.: WO2010/138271
PCT Pub. Date: Dec. 2, 2010

(65) Prior Publication Data
US 2012/0116144 A1    May 10, 2012

Related U.S. Application Data

(60) Provisional application No. 61/182,466, filed on May 29, 2009, provisional application No. 61/256,383, filed on Oct. 30, 2009.

(51) Int. Cl.
*C07C 7/12* (2006.01)

(52) U.S. Cl.
USPC .............................. 585/821; 585/828; 585/826

(58) Field of Classification Search
None
See application file for complete search history.

(56) References Cited

U.S. PATENT DOCUMENTS

| | | |
|---|---|---|
| 5,457,260 A | 10/1995 | Holt |
| 5,470,480 A | 11/1995 | Gray et al. |
| 5,470,482 A | 11/1995 | Holt |
| 5,684,580 A | 11/1997 | Cooper et al. |
| 5,902,486 A | 5/1999 | Couenne et al. |
| 6,072,576 A | 6/2000 | McDonald et al. |
| 6,162,644 A | 12/2000 | Choi et al. |
| 6,217,774 B1 | 4/2001 | Nagamatsu et al. |
| 6,332,982 B1 | 12/2001 | Hotier et al. |
| 6,471,870 B1 | 10/2002 | Nicoud et al. |
| 6,652,754 B1 | 11/2003 | Pavone |
| 7,192,526 B2 | 3/2007 | Couenne et al. |
| 7,326,823 B2 | 2/2008 | Williams et al. |
| 7,582,207 B2 | 9/2009 | Hotier et al. |
| 2007/0119783 A1 | 5/2007 | Nicolas et al. |

FOREIGN PATENT DOCUMENTS

| | | |
|---|---|---|
| EP | 0 479 472 | 4/1992 |
| WO | 03/059852 | 7/2003 |

*Primary Examiner* — Tam N Nguyen
(74) *Attorney, Agent, or Firm* — Andrew B. Griffis

(57) ABSTRACT

There is provided a closed loop purity and recovery control system and process for operating a xylene purification system such as a Parex unit.

14 Claims, 1 Drawing Sheet

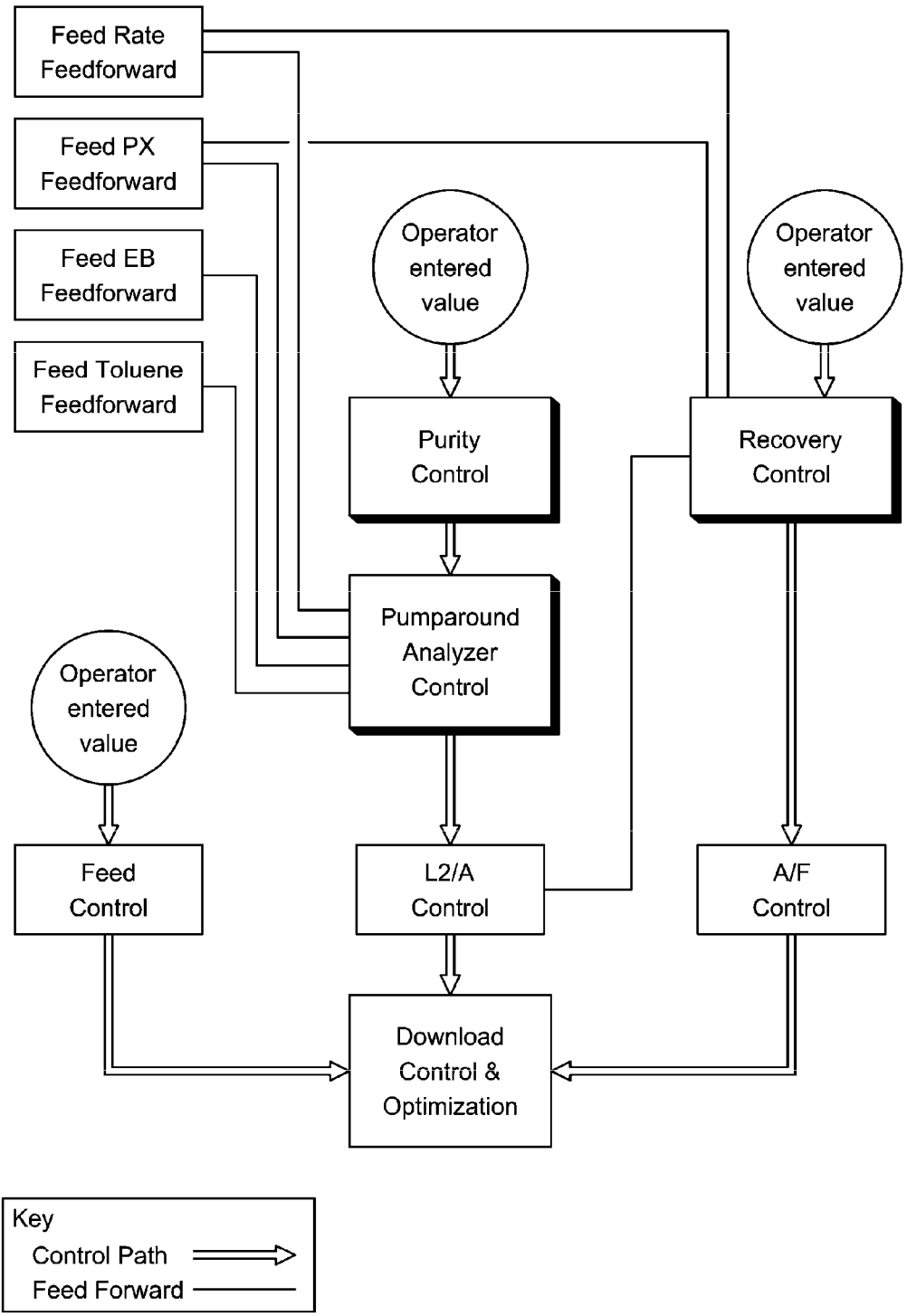

FEEDBACK AND FEEDFORWARD CLOSED LOOP PURITY AND RECOVERY CONTROL

CROSS REFERENCE TO RELATED APPLICATIONS

This application is a National Stage Application of International Application No. PCT/US2010/033088, filed Apr. 30, 2010, which claims priority to Provisional Application No. 61/256,383, filed Oct. 30, 2009 and Provisional Application No. 61/182,466, filed May 29, 2009, the disclosures of which are incorporated by reference in their entireties.

FIELD OF THE INVENTION

The invention relates to purity and recovery control in the production of xylenes and more particularly to a process for producing high-purity paraxylene.

BACKGROUND OF THE INVENTION

Continuous separation processes for the selective adsorption of para-xylene from a mixture of other xylene isomers, ethylbenzene, and non-aromatic hydrocarbons are common in industry. Generally, the processes use a solid adsorbent which preferentially retains the para-xylene in order to separate the para-xylene from the rest of the mixture. Often, the solid adsorbent is in the form of a simulated moving bed, where the bed of solid adsorbent is held stationary, and the locations at which the various streams enter and leave the bed are periodically moved. The adsorbent bed itself is usually a succession of fixed sub-beds. The shift in the locations of liquid input and output in the direction of the fluid flow through the bed simulates the movement of the solid adsorbent in the opposite direction. Moving the locations of liquid input and output is accomplished by a fluid directing device known generally as a rotary valve which works in conjunction with distributors located between the adsorbent sub-beds. The rotary valve accomplishes moving the input and output locations through first directing the liquid introduction or withdrawal lines to specific distributors located between the adsorbent sub-beds. After a specified time period, called the step time, the rotary valve advances one index and redirects the liquid inputs and outputs to the distributors immediately adjacent and downstream of the previously used distributors. Each advancement of the rotary valve to a new valve position is generally called a valve step, and the completion of all the valve steps is called a valve cycle. The step time is uniform for each valve step in a valve cycle, and is generally from about 60 to about 120 seconds, such as 90 seconds. A typical process contains 24 adsorbent sub-beds, 24 distributors located between the 24 adsorbent sub-beds, two liquid input lines, two liquid output lines, and associated flush lines.

The principal liquid inputs and outputs of the adsorbent system consist of four streams: the feed, the extract, the raffinate, and the desorbent. Each stream flows into or out of the adsorbent system at a particular flow rate, and each flow rate is independently controlled. The feed, which is introduced to the adsorbent system, contains the para-xylene (PX) which is to be separated from other components in the feed stream, which typically include ethylbenzene (EB), metaxylene (MX), orthoxylene (OX), toluene, various C9+ aromatics, and non-aromatics. The desorbent, which is introduced to the adsorbent system, contains a liquid capable of displacing feed components from the adsorbent. The extract, which is withdrawn from the adsorbent system, contains the separated para-xylene which was selectively adsorbed by the adsorbent, and desorbent liquid. The raffinate, which is withdrawn from the adsorbent system, contains the other xylene isomers, ethylbenzene, non-aromatic hydrocarbons which were less selectively absorbed by the adsorbent, and desorbent liquid. There also may be associated flush streams introduced to and withdrawn from the adsorbent system. These flush streams can vary in composition and rate and can include but are not limited to paraxylene, ethylbenzene, metaxylene, orthoxylene, and desorbent. The flush flow rates are typically independently controlled. The four principal streams are spaced strategically throughout the adsorbent system and divide the sub-beds into four major zones, each of which performs a different function.

Zone I contains the adsorbent sub-beds located between the feed input and the raffinate output, and selective adsorption of the para-xylene takes place in this zone. Zone II contains the adsorbent sub-beds located between the extract output and the feed input, and the desorption of components other than para-xylene takes place in this zone. Zone III contains the adsorbent sub-beds located between the desorbent input and the extract output, and the para-xylene is desorbed in this zone. Finally, Zone IV contains the adsorbent sub-beds located between the raffinate output and the desorbent input, and the purpose of this zone is to prevent the contamination of the para-xylene with other components. The flush flows are introduced in the sub-beds of some of the major zones and create minor zones which are a function of the major zone rates and the smaller flush flow rates.

Two other important streams are the pumparound and pusharound streams. In a typical para-xylene separation process the adsorbent bed consisting of 24 sub-beds is split into two main chambers. One chamber contains sub-beds 1 through 12 and the other contains sub-beds 13 through 24. Although functionally the adsorbent system as a whole does not have a top or a bottom, each chamber has a physical top and bottom. The pumparound and pusharound streams each conduct the liquid effluent exiting the physical bottom of one adsorbent bed chamber back up to reenter the physical top of the other adsorbent bed chamber. The pumparound stream is the stream that conducts the effluent of sub-bed 24 from the physical bottom of the second chamber to reenter sub-bed 1 at the physical top of the first chamber. The pusharound stream conducts the effluent of sub-bed 12 from the physical bottom of the first chamber to reenter sub-bed 13 at the physical top of the second chamber. It is important to note that the composition of the pumparound or pusharound stream changes with each valve step, and in one valve cycle both streams will have sequentially carried the composition which corresponds to each valve position.

In this regard, see U.S. Pat. No. 5,470,480 and references cited therein.

The common practice in industry is to control the paraxylene simulated moving bed separation process either by on-line gas chromatography analyses, by off-line laboratory analyses of the product streams or by online gas chromatography of the product streams. When controlling on-line, the gas chromatography analysis of the pumparound stream generally requires about 10 minutes which is considerably greater than the usual step time of the rotary valve. Therefore, only select valve positions may be sampled and analyzed. Generally, only Zone II and Zone IV are sampled and analyzed. The data provided by this on-line gas chromatography procedure is useful for detecting process upsets, but unfortunately analyzing the composition of only two valve positions provides limited information regarding the performance of the separation process.

A more thorough control is accomplished using off-line laboratory gas chromatography analyses to determine the values of the concentrations of the components in samples of the pumparound stream taken at each valve position in a valve cycle. The measured concentrations are then plotted versus their relative valve positions to form what is generally called a profile. Using the profile, the recovery and purity of the para-xylene can be calculated and the degree of optimization of the separation may be visually assessed. Then required changes in the step time and liquid stream flow rates may be determined and implemented. The drawbacks to controlling a separation process in this fashion are the time delay between sampling and analytical results where the latter are used to determine whether or what changes should be made, the labor involved to manually collect the stream samples, and the personal exposure of the operator manually collecting the stream samples. Since the analyses are performed off-line, the time delay may be from one to several days long. Because of the drawbacks, refiners generally only perform this procedure infrequently to determine the health of the separation process, such as about once every six months, or if there is a problem with the separation process.

Other separation processes, such as the separation of oil from wax, have been controlled using spectroscopic determinations of impurities in the separated pure product. For instance, the Canadian Patent Application 2,050,108 disclosed spectroscopically measuring one component of a mixture in another component of the mixture following the separation of the mixture into its components. The results of the measurements are used to control the separation so that the amount of impurity in the pure product is controlled to a desired value.

A paraxylene process such as described above can be controlled in an open loop fashion where the operator adjusts process parameters based on the product purity and product recovery analyzers. There is a time lag between parameter adjustments and final product purity and recovery due to the process. Due to normal variations in feed rate, feed composition, and other variables, the operator leaves a cushion between the target purity and recovery and the actual product purity and product recovery. This cushion requires more energy and can limit production.

Additional relevant patents are U.S. Pat. Nos. 5,470,482; 5,457,260; 6,072,576; 6,162,644; 6,217,774; 7,192,526; and U.S. Patent Application Publication Nos. 20060006113 and 20070119783.

The present inventors have recently described the use of analyzers in the Parex process using predictive models in U.S. Provisional Application No. 61/182,466, filed 29 May 2009. As described therein, a process control application can be constructed that automatically adjusts the process parameters to meet the product purity and recovery targets. The application also uses the analyzers to adjust the parameters to correct any prediction errors. Because the controller can decrease variability in the product purity and recovery, the targets can be run closer to the purity specification and recovery needs. This saves energy and can increase production.

The present inventors have now discovered an improved feedforward algorithm including an adjustment to one of the controlled variable values for feed composition with improved corrective controls that automatically adjusts parameters to decrease variability in product purity.

SUMMARY OF THE INVENTION

According to the invention, there is provided a feedback and feedforward closed loop purity and recovery control system and process for operating a system, such as a Parex Unit, that uses analyzers along with predictive models, to provide a process control system that automatically adjusts parameters to correct for any predictive errors to decrease variability in product purity.

One or more product analyzers which measure impurities selected from ethylbenzene (EB), metaxylene (MX), orthoxylene (OX), toluene (TOL), non-aromatics (NA), paradiethylbenzene (PDEB), and any C9+ material, and mixtures thereof, are used to calculate product purity of the target product, which in the well-known Parex™ Process is paraxylene (PX). The analyzer may also include a paraxylene analyzer in the raffinate system or in the raffinate tower system and/or a paraxylene analyzer in the feed system to calculate product recovery. It also uses the same or different analyzer in the sieve process to predict product purity.

In embodiments, the application outputted to two parameters (though not limited to two) that adjust the sieve operation.

In other preferred embodiments, one or more feed purity analyzer components, feed rate, a recycle composition, and flush rate(s), which are used in a feedforward fashion to predict changes in sieve operation, the product purity, and the product recovery. The application adjusts the sieve parameters based position of feed location within the sieve system analyzer, a pumparound analyzer, a pusharound analyzer, or a combination thereof, the feedforward variables, and the feedback purity and recovery calculations.

Determinations of the real-time (i.e., "current") values are generally made spectroscopic ally. In preferred embodiments the measurements are made for every valve position, but that can be made for every other valve position or some other periodic or even random selection of measurements.

In preferred embodiments of any of the aforementioned embodiments, the values of the concentrations of one or more of the solutes are measured at each valve step and the results plotted versus the relative positions of the valve to generate a profile, which can be used to make predictive models and/or troubleshoot the process. In another embodiment, the values of the concentrations from a single step can be used.

In other embodiments of any of the aforementioned embodiments, one or two of steps (I), (II), and (III), and one or more of the subroutines, steps (a) through (d), steps (e) through (h), or steps (i) through (l) can be omitted. This is particularly useful if an analyzer (or more than one analyzer) is not available and/or if only part of the system is operational for whatever reason.

As with many control schemes, there are process constraints that should be observed for preferred operation. Thus, in preferred embodiments of the present invention, there can be minimum and maximum values for any process variable that should be respected. There can also be a rate of change limit put on changes to process parameters, there can be a limit to how frequently a parameter adjustment is made by the control scheme, and so forth. The control scheme according to the present invention can be limited based on such constraints and can allow for optimization of the parameters to the constraint limits.

The values of the process values used in the controller can also be filtered to smooth out the changes to the process parameters. The filter algorithms should be set up to minimize normal signal noise without loosing the "real" information in the variations of the variables. Those skilled in the art are aware of many filtering techniques that can be used.

These and other objects, features, and advantages will become apparent as reference is made to the following detailed description, preferred embodiments, examples, and appended claims.

BRIEF DESCRIPTION OF THE DRAWING

FIG. 1 is a schematic illustrating an embodiment of the invention and is not intended to be limiting.

DETAILED DESCRIPTION

According to the invention, there is provided a feedback and feedforward closed loop purity and recovery control system and process for operating said system.

In embodiments, there is a process of continuously controlling at least one characteristic of a para-xylene separation process containing a simulated moving adsorbent bed.

In general terms, the characteristic, which has an initial value, $V_i$, (or for convenience, Vi) and target or desired value, $V_f$ (or for convenience Vf). It is not necessary nor, in embodiments, desirable to select a variance from the target value, $\delta$, such as suggested in the prior art as represented in the Background section. In embodiments, the process operates so as to move Vi toward Vf continually.

The system is controlled through measuring the concentrations of the components in the pumparound or pusharound stream in at least one valve position of the rotary valve cycle, and determining the necessary changes in the values of the step time and liquid stream flow rates in order to achieve the target value of the characteristic by applying a suitable algorithm to the values either manually or with the aid of a computer.

The liquid streams whose flow rates may be adjusted are primarily the feed stream, the extract stream, the raffinate stream, the desorbent stream, and the zone flows. The flow rates of the associated flush streams may also be adjusted. The components whose concentrations are measured are generally but not restricted to para-xylene, other xylene isomers, ethylbenzene, and non-aromatic hydrocarbons. The algorithm relates changes in the value of the characteristic to changes in the step time and flow rates with resulting changes in the values of the concentrations of the components at each valve position measured. Applying an algorithm determines the required changes in the step time and flow rates to produce a new value of the characteristic, $V_N$, which is preferably numerically closer to the target value. This progression can be represented as $|V_f - V_N| \leq |V_f - V_i|$. The step time and flow rates are then adjusted as required, preferably automatically, and the control process is repeated as desired by the operator or as controlled automatically. It is important to note that while it is preferred to adjust the flow rates and the step time, it is not necessary to adjust both. It is possible to adjust only the flow rates and still control the characteristic.

The present inventors have found that process control for a dynamic system (like Parex) according to the present invention provides better results than a statistical control or delta control approach as described in the prior art described above. The process control system takes can take advantage for feedforward information and makes a decision to change an output even if the actual value of the control parameter is equal to the target of that control parameter. The process control system also takes advantage of the previous and/or expected values of the control parameter even if the difference between the actual value of the control variable and the target of the control variable is small or zero. The delta control approach (including statistical control) in which a difference between the actual value of the control variable and the target value (delta) is evaluated to decide the output of the control will not work as well because it does not take advantage of the previous and/or expected values of the controlled variable. This could lead to cycling or sluggish response. Delta control without feedforward control does not anticipate changes that are coming which would lead to poor control of the actual value.

Also important in embodiments is that EB, MX, and OX concentrations (or some other characteristic of these species) be taken into account. A Parex unit separates paraxylene (PX) for ethyl benzene (EB), metaxylene (MX), and orthoxylene (OX) among other impurities. The present inventors have also discovered that, in combination with process control, a controller that controls for purity that takes into account EB, MX, and OX will be better than a controller that controls just EB. This is because there are changes in the Parex plant that have different effects on EB vs MX or OX. If only EB is controlled, the total purity which also include MX and OX will not be correct, and the effect is synergistic and not just additive.

The characteristics controlled are generally the purity of the para-xylene product stream and the recovery of para-xylene from the feed stream into the extract stream. The characteristics may be either measured or calculated. The preferred embodiment is to calculate the theoretical values of the characteristics from the measurements of the concentrations of the components since the actual measurements may involve variables introduced at locations other than in the actual separation. Such calculations are common, and are generally known to those skilled in the art. Either the purity or the recovery may be controlled, or both may be controlled simultaneously, and, as discussed earlier, the control may be to achieve either a target value of the characteristic or to maximize or minimize the value of the characteristic.

The pumparound and pusharound streams are the preferred locations to perform the measurements of the concentrations of components since with every step of the rotary valve, these streams carry a new composition corresponding to the relative position of the valve. In one complete valve cycle the stream will have sequentially carried the composition corresponding to each relative position of the valve. Generally, only one stream, either the pumparound or the pusharound, is measured. Which is chosen is not important to the success of the invention and the choice may be based on convenience. In embodiments, once the choice is made, the chosen stream is to be used for at least one complete valve cycle. In embodiments, the components whose concentrations are measured in the pumparound or pusharound stream are those which are necessary to calculate the characteristic of interest.

The concentrations of the components in the pumparound and pusharound streams can be measured by any suitable analytical technique. It is preferable that the analysis time is less than the step time of the rotary valve, generally about 60 to 120 seconds, such as 90 seconds. The preferred analytical technique is spectroscopy. Spectroscopic determinations of the values of the concentrations of the components in the pumparound or pusharound stream pursuant to this invention are made by first measuring the absorption, reflectance, or transmission spectrum of the pumparound or pusharound stream and then calculating the values of said concentrations according to a predetermined algorithm relating said concentrations of said components to the spectrum.

It has been found that using an instrument capable of making a single measurement using a portion of the both the NIR and Mid-Infrared regions produces superior results as compared to a spectrometer which is dedicated to a single measurement region such as NIR or Mid-Infrared. It has also been determined that superior results can be obtained by using two or more models for key components, with different wavelength ranges for each model, produces superior results. The control system preferably will automatically select the appropriate model based on each models optimized measurement range. This may be accomplished by one of skill in the art in possession of the present disclosure.

Such optical measurements are known in the art, as are several mathematical algorithms for analyzing the spectral data including but not limited to, partial least squares with latent variables, multiple linear regression, and principal component regression.

In embodiment, the preferred mathematical method to develop the regression models is through the use of the "Constrained Principal Spectral Analysis" technique set forth in U.S. Pat. No. 5,121,337. One of skill in the art may also wish to consult references such as Martens, H.; Naes, T. In Multivariate Calibration by Data Compression; Williams, P.; Norris, K. Eds.; Near Infrared Technology in the Agricultural and Food Industries; Amer. Assoc. Cereal Chemists St. Paul; Chapter 4. Applying NIR or FT-IR spectroscopy, for optimization with regard to multivariate analysis.

In embodiments, the spectroscopy can be performed on-line, where the sample is automatically routed from the pumparound or pusharound stream to the spectrophotometer, or in-line, where a probe is placed directly in the pumparound or pusharound stream. The data is available in less than a minute, which when used in the present invention translates into the ability to immediately and precisely control the value of a characteristic.

The preferred embodiment of the invention is that where the concentration of the components in the pumparound or pusharound stream are measured at every valve position.

As is commonly known by those skilled in that art, random noise in spectroscopy measurements may be reduced by repeatedly measuring the spectrum and performing spectral averaging. Therefore, to increase the precision of the measurements, this invention embodies the situation where the set of concentrations of components corresponding to a given valve position is the average of repeated measurements made while the valve was in that position. The plurality of measurements are preferably made on the dynamic flowing pumparound or pusharound stream so that the average represents the average concentrations of the components over the duration of the valve step or a portion of the valve step. It is further understood that, where appropriate, the measurements of the dynamic flowing stream within one valve step may be used to determine the profile of the concentrations of the components over the duration of the valve step instead of being averaged. It is also contemplated that a static sample from the pumparound or pusharound stream contained in a suitable sample cell could be measured repeatedly and averaged. The results of the static measurements would be particular to one point within the valve step, as opposed to an average over the duration of the valve step.

For the preferred embodiment, how many measurements may be taken within a valve step depends upon the speed of the analyzer and the step time of the rotary valve. For example, if the step time is 60 seconds, and the analysis time for the spectroscopy measurement is 6 seconds, a maximum of 10 spectra may be measured before the valve advances. If the maximum number of measurements possible within the step time provides insufficient precision, a static sample may be used, and the number of measurements may be increased. The consequence, however, is that under these circumstances not every valve position may be measured. For purposes of this invention, the number of valve positions for which measurements are required is less than four.

In the preferred embodiment where the values of the concentrations of the components are measured at each valve step, the results of the measurements may be plotted versus the relative positions of the valve to generate a profile. While generating such a profile is not necessary, it does provide additional advantages. By inspecting the profile, an operator may be able to learn troubleshooting information such as whether there has been a process upset, the adsorbent has been poisoned, or whether the degree of adsorbent hydration is correct. As the number of valve positions measured decreases from the preferred, the profile may still be plotted, but it becomes less useful and less information such as described above may be obtained.

Once the values of the concentrations of the components in the pumparound or pusharound stream for one valve cycle have been collected, a suitable algorithm may be applied to determine the required changes in the step time and/or liquid stream flow rates to effect a desired change in the characteristic controlled. Suitable algorithms may be any of those commonly used including linear models, first order plus deadtime models, commercially available multivariable controllers, multivariate regression, neural network modeling, and the like. Numerous commercial programs, per se well-known in the art, are available. The algorithm may be applied manually or preferably with the aid of a computer.

The step time and liquid stream flow rates are then adjusted as required. The required adjustments may be in any combination. For example, only one liquid stream flow rate may be adjusted, all streams may be adjusted, or any group may be adjusted. Furthermore, the direction and degree of adjustment required for each stream flow rate may be different. For example, while one flow rate may be increased substantially, another flow rate may be slightly decreased. Also, the combination of flow rate adjustments may be accompanied by a step time adjustment. The step time may be adjusted to a longer time or to a shorter time. Very often, one variable may be adjusted to a required new value, and as a consequence others may be changed in order to keep various process conditions constant.

The adjustments may be made manually, or automatically. The preferred method is to perform the adjustments automatically. The entire control procedure may then be repeated. After the target value of the characteristic has been achieved or the value of the characteristic has been adjusted to the desired value, the control process may simply continue but without making adjustments until the value of the characteristic falls outside the acceptable range. Alternatively, the process may be repeated only periodically in order to monitor the characteristic.

The invention may be better understood by reference to FIG. 1, which is a schematic illustration of an embodiment according to the present invention and should not be taken as limiting. One of skill in the art would recognize, in light of the entire disclosure, that numerous modifications can be made.

FIG. 1 is a schematic view of the basic control structure in an embodiment of the invention. The Pumparound Analyzer Control, Purity Control, and Recovery Control can advantageously be heuristic model based controllers that control (1) Final Product Purity, (2) an Intermediate level of multiple components in the Parex Process, and (3) Unit recovery. The model based controller may be a standard model based controller that is well-known in the art per se. These controllers output to Parex process operating parameters such as L2/A (ratio of zone II flow to Adsorbent flow) and feed rate, A/F (ratio of Adsorbent/Total Aromatics Feed) that are downloaded into the process. This download changes various flows and a timer in the Parex Process. There is a model based relationship between each controller and the variable that the controller outputs to. This feedback control logic uses the target values and the actual controller values versus the predictions of the controller values based on the changes in the variables that the controller outputs to.

For example, if the A/F changes in a standard step change fashion, the Recovery eventually changes to a new value with some dynamics. It is the ultimate change in A/F vs Recovery and the dynamics of the Recovery change that are used in the model to predict the outcome of the Recovery. If the prediction and the actual values of Recovery don't match, or if the Recovery target is changed, adjustments to the A/F are made to bring the Recovery to its target.

There are also feedforward variables, as shown in FIG. 1, that when taken into account can minimize disturbances to the controlled variables. For example, if the Feed PX changes, then the Pumparound Analyzer Controller will sense that and change the L2/A variable in a predicted feedforward fashion to mitigate the impact on the Pumparound Analyzer value.

Plant tests are used to determine the relationships between the model based controllers and the variables that the controllers manipulate. As explained above, with the plant steady, a step change is made in manipulated variable (such as A/F) and the response of the controlled variable (such as Recovery) is measured. The mathematical relationship between the step and the response is used in the model based controllers. Plant tests are also used to determine the relationship between the model based controllers and the feedforward variables. Note that depending on the plant needs, there can be additional controllers, manipulated variables, and feedforward variables.

The toluene in the pumparound can interfere with the EB peak depending on the type of analyzer. For example, an FTIR can "see" toluene and report it as EB raising the reported value of EB. A correction for the P/A model based controller reading is made based on the toluene in the feed to the unit. Thus if the toluene in the feed changes, this impact is backed out of the EB reading through a simple gain.

In the process described in FIG. 1, there are limits for certain process variables and there are other constraints that the controllers should not violate. The DOWNLOAD & CONTROL OPTIMIZATION block in the FIG. 1 keeps track of the unit constraints and will not allow a download that would violate those constraints. This block can be used to optimize the unit up to one or more of the process constraints.

Many of the signals used in the control scheme are filtered as described above to smooth out the changes to the process made by the DOWNLOAD & CONTROL OPTIMIZATION block.

The invention has been described above with reference to specific details and embodiment which, it will be understood by one of ordinary skill in the art, are intended to be exemplary and not limiting. Accordingly, the invention can be practiced other than as specifically set forth herein.

Trade names where used are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention.

What is claimed is:

1. A process comprising separating a solute from a stream whose composition contains at least the solutes paraxylene (PX), orthoxylene (OX), metaxylene (MX), and ethylbenzene (EB), using a simulated moving bed comprising plural beds and having multiple input and output streams each with individual flow rates, a step time, multiple valve positions, and a pumparound and/or pusharound stream, said process including control of a value of a characteristic of said pumparound and/or pusharound stream, VPAc, to a desired value VPAf using model based control with predictive feedforward, controlling the characteristic value VRc of the recovery of the solute to a desired value VRf, using model based control with predictive feedforward, controlling the characteristic value VPc of the product purity to a desired value VPf, using model based control with predictive feedforward control, said process comprising the steps of at least one of (I), (II) and (III), including substep routines (a) through (d), (e) through (h), and (i) through (l), respectively:

(I) (a) determining VPAc from information including at least one of on-line sampling and in-line sampling of the current concentrations of at least one of said solutes in said pumparound and/or pusharound streams at a specific time after a valve position change for at least one valve position within said one or more valve cycles; then (I) (b) comparing VPAc and VPAf; and (I) (c) adjusting at least one parameter selected from the step time and the flow rates of at least one stream in the process, according to a pre-determined model based algorithm, said algorithm relating a change in the current value of the characteristic to changes in said at least one parameter and VPAf; then after at least one step (a), step (b) and step (c), (I) (d) repeating at least one step (a), step (b), and step (c); and (II) (e) determining VRc from information including at least one of on-line sampling, in-line sampling, and at least one flow meter, of the current concentrations of at least one of said solutes in at least one stream in the process; then (II) (f) comparing VRc and VRf; then (II) (g) adjusting at least one parameter selected from the step time and the flow rates of at least one stream in the process, according to a predetermined algorithm, said algorithm relating a change in the current value of the characteristic to changes in said at least one parameter and VRf; then after at least one step (e), (f) and (g), (II) (h) repeating at least one step (e), step (f) and step (g); and (III) (i) determining VPc from including at least one of on-line sampling, in-line sampling, and offline sampling, of the current concentrations of at least one of said solutes in at least one stream in the process; then (III) (j) comparing VPc and VPf; then (III) (k) adjusting at least one parameter selected from VPAf, the step time, and the flow rates of at least one stream in the process, according to an algorithm, said algorithm relating a change in the current value of the characteristic to changes in said at least one parameter and VPf; then (III) (l) repeating at least one step (i), (j), (k).

2. The process of claim 1, including at least two of steps (I), (II), and (III), including said subroutines.

3. The process of claim 1, including all three of steps (I), (II), and (III), including said subroutines.

4. The process of claim 1, including repeating the same step or steps, including said subroutines.

5. The process of claim 1, wherein said process is the process of separating paraxylene (PX) from said solutes.

6. The process of claim 1, wherein where values of process constraints are respected by the download controller.

7. The process of claim 6, wherein said process constraints include the minimum time between downloads and a limit to how much a download parameter can be optimized.

8. The process of claim 1, including analyzing said pumparound and/or pusharound stream with a GC analyzer.

9. The process of claim 1, including analyzing said pumparound and/or pusharound stream with an IR analyzer.

10. The process of claim 1, including step (I) (c), step (I) (c) including a feedforward action from at least one other process variable.

11. The process of claim 10, wherein said at least one other variable is the concentration of toluene used to adjust the value of VPAc.

12. The process of claim 1, including step (II) (g), step (II) (g) including a feedforward action from at least one other process variable.

13. The process of claim 1, including step (III) (k), step (III) (k) including a feedforward action from at least one other process variable.

14. The process of claim 1, said process including a step of adjusting the flow rate of at least one stream selected from the group consisting of feed stream, extract stream, raffinate stream, and desorbent stream.

* * * * *